(12) United States Patent
Carter et al.

(10) Patent No.: US 8,759,767 B2
(45) Date of Patent: Jun. 24, 2014

(54) COMBINED RAMAN AND IR FIBER-BASED SENSOR FOR GAS DETECTION

(75) Inventors: Jerry C. Carter, Livermore, CA (US);
James W. Chan, Elk Grove, CA (US);
James E. Trebes, Livermore, CA (US);
Stanley M. Angel, Columbia, SC (US);
Boris Mizaikoff, Ulm (DE)

(73) Assignees: Lawrence Livermore National Security, LLC, Livermore, CA (US); University of South Carolina, Columbia, SC (US); Georgia Tech Research Corporation, Atlanta, GA (US)

( * ) Notice: Subject to any disclaimer, the term of this patent is extended or adjusted under 35 U.S.C. 154(b) by 971 days.

(21) Appl. No.: 12/545,566

(22) Filed: Aug. 21, 2009

(65) Prior Publication Data
US 2012/0105827 A1 May 3, 2012

Related U.S. Application Data

(60) Provisional application No. 61/090,662, filed on Aug. 21, 2008.

(51) Int. Cl.
*G01N 21/35* (2006.01)
(52) U.S. Cl.
USPC ............................................... 250/338.1
(58) Field of Classification Search
USPC ...................................................... 250/338.1
See application file for complete search history.

(56) References Cited

U.S. PATENT DOCUMENTS

| | | | | |
|---|---|---|---|---|
| 4,676,639 A | * | 6/1987 | Van Wagenen | 356/246 |
| 4,709,150 A | * | 11/1987 | Burough et al. | 250/338.1 |
| 4,802,761 A | | 2/1989 | Bowen et al. | |
| 4,953,976 A | * | 9/1990 | Adler-Golden et al. | 356/301 |
| 5,060,508 A | * | 10/1991 | Wong | 73/31.02 |
| 5,110,204 A | * | 5/1992 | Miles et al. | 356/28 |
| 5,163,332 A | * | 11/1992 | Wong | 73/863.23 |
| 5,222,389 A | * | 6/1993 | Wong | 73/31.02 |
| 5,351,120 A | * | 9/1994 | Jurcik et al. | 356/246 |
| 5,521,703 A | * | 5/1996 | Mitchell | 356/301 |
| 5,583,877 A | * | 12/1996 | MacPherson et al. | 372/4 |
| 5,831,730 A | * | 11/1998 | Traina et al. | 356/336 |
| 6,294,389 B1 | * | 9/2001 | Vitale et al. | 436/57 |
| 6,486,474 B1 | * | 11/2002 | Owen et al. | 250/339.02 |
| 6,527,398 B1 | * | 3/2003 | Fetzer | 356/437 |
| 6,953,487 B2 | * | 10/2005 | Cliche et al. | 29/623.2 |
| 8,218,139 B2 | * | 7/2012 | Milosevic et al. | 356/301 |

(Continued)

OTHER PUBLICATIONS

Renishaw, Combined Raman and FT-IR spectroscopy, Apr. 2004, SPD/AN/101 issue 1.1.*

(Continued)

*Primary Examiner* — David Porta
*Assistant Examiner* — Djura Malevic
(74) *Attorney, Agent, or Firm* — John P. Wooldridge (57) ABSTRACT

A double-pass fiber-optic based spectroscopic gas sensor delivers Raman excitation light and infrared light to a hollow structure, such as a hollow fiber waveguide, that contains a gas sample of interest. A retro-reflector is placed at the end of this hollow structure to send the light back through the waveguide where the light is detected at the same end as the light source. This double pass retro reflector design increases the interaction path length of the light and the gas sample, and also reduces the form factor of the hollow structure.

20 Claims, 5 Drawing Sheets

(56) References Cited

U.S. PATENT DOCUMENTS

| | | | |
|---|---|---|---|
| 8,294,898 B2* | 10/2012 | Qu et al. | 356/437 |
| 2007/0145275 A1* | 6/2007 | Wong | 250/339.13 |
| 2008/0212216 A1* | 9/2008 | Milosevic et al. | 359/850 |
| 2009/0059235 A1* | 3/2009 | Qu et al. | 356/437 |
| 2009/0213380 A1* | 8/2009 | Appel et al. | 356/437 |
| 2010/0201977 A1* | 8/2010 | Milosevic et al. | 356/301 |

OTHER PUBLICATIONS

Berg, J.M. et al., "Performance of Fiber-Optic Raman Probes for Analysis of Gas Mixtures in Enclosures", Appl. Spec., vol. 56, No. 1, 2001, pp. 83-90.

Charlton, C., et al., "Hollow-waveguide gas sensing with room-temperature quantum cascade lasers", IEE Proc. Optoelectron., vol. 150, No. 4, Aug. 2003, pp. 306-309.

Harrington, J.A., et al., "Review of hollow waveguide technology", SPIE vol. 2396, pp. 4-14. Dated: May 1995.

Kosterev, A.A, et al., "Methane concentration and isotopic composition measurements with a mid-infrared quantum cascade laser", Optics Letters, vol. 24, No. 23, Dec. 1999, pp. 1762-1764.

Lancaster, D.G., et al., "High-power continuous-wave mid-infrared radiation generated by difference frequency mixing of diode-laser-seeded fiber amplifiers and its application to dual-beam spectroscopy", Optics Letters, vol. 24, No. 23, Dec. 1999, pp. 1744-1746.

Lancaster, D.G., et al., "Portable fiber-coupled diode-laser-based sensor for multiple trace gas detection", Appl. Phys., B 69, 1999, pp. 459-465.

Lancaster, D.G., et al., "Real-time measurements of trace gases using a compact different-frequency-based sensor operating at 3.5µm", Appl. Phys., B 67, 1998, pp. 339-345.

Mine, Y., et al., "Detection of formaldehyde using mid-infrared difference-frequency generation", Appl. Phys, B 65, 1997, pp. 771-774.

Petrov, K.P., et al., "Compact laser difference-frequency spectrometer for multicomponent trace gas detection", Appl. Phys., B 66, 1998, pp. 531-538.

Petrov, K.P., et al., "Precise measurement of methane in air using diode-pumped 3.4-µm difference-frequency generation in PPLN", Appl. Phys., B 64, 1997, pp. 567-572.

Richter, D., et al., "Compact mid-infrared trace gas sensor based on different-frequency generation of two diode lasers in periodically poled LiNb03", Appl. Phys., B 67, 1998, pp. 347-350.

Richter, D., et al., "Tunable, fiber coupled spectrometer based on difference-frequency generation in periodically poled lithium niobate", OSA/ASSL, 1999, pp. 1-4.

Tittel, F.K., et al., "Laser based absorption sensors for trace gas monitoring in a spacecraft habitat", 99ES-102, Society of Automotive Engineers, Inc., 1999, http://www.ruf.rice.edu/~lasersci, 9 pp.

Töpfer, T., et al., "Room-temperature mid-infrared laser sensor for trace gas detection", Appl. Optics, vol. 36, No. 30, Oct. 1997, pp. 8042-8049.

\* cited by examiner

COMBINED RAMAN AND IR FIBER-BASED SENSOR FOR GAS DETECTION

This application claims priority to provisional application No. 61/090,662, titled: "A Combined Raman and IR Fiber-Based Sensor for Gas Detection" filed Aug. 21, 2008.

The United States Government has rights in this invention pursuant to Contract No. DE-AC52-07NA27344 between the United States Department of Energy and Lawrence Livermore National Security, LLC.

BACKGROUND OF THE INVENTION

1. Field of the Invention

The present invention relates to gas analysis via spectroscopy, and more specifically, it relates to the use of infrared absorption and Raman scattering spectroscopy and assays for the qualitative and quantitative analysis of gases.

2. Description of Related Art

Gas detection utilizing Raman spectroscopy has previously been demonstrated using a solid-core optical fiber probe, typically comprised of one or more optical fibers for excitation and signal collection. These probes provide a conduit (e.g., light pipe) for exciting a gas or a gas mixture under test with an excitation wavelength(s) of light that generates Stokes and/or anti-Stokes scattering, part of which is collected by a signal collection fiber(s) and provided to a spectrometer. Wavelength cross-sections for gas species have been documented. The main technical problem with this approach is the low signals that are generated from the gas analyte because of the low Raman scattering cross-sections and potential background interferences. This severely limits the sensitivity level, making gas detection at low ppm levels difficult. Studies have used a multi-pass cell or cavity, as well as optical fiber multi-pass cells, to increase the interaction path length between the gas molecules and excitation photons, which improves the limits of detection. However, implementing this cavity design in the field for gas detection is difficult because it requires delicate and precise alignment, a small size, and lacks long-term robustness and rigidity.

Chemical detection using optical spectroscopic techniques frequently requires significant enhancement of the signals in order to achieve detection limits of parts per million (ppm) levels. As mentioned above, one standard approach is the use of multi-pass cavities that maximize the interaction length between the chemical analyte and the excitation light. The cavity usually consists of two mirrors that reflect the light back and forth. Two parabolic mirrors can be used to focus multiple reflections to the same point. Field deployment of these devices is difficult because of the sensitivity of their optical alignment. Due to the limitations and difficulties of using multi-pass configurations in the field, utilizing optical fiber is frequently more suitable under these conditions. Work in this area has largely focused on solid-core optical fiber probes (such as e.g. Raman gas sensing with fiber optic probes). Fiber based IR absorption spectroscopy for trace gas detection has previously been demonstrated. As in the Raman techniques described above, the fiber geometries used for IR absorption spectroscopy are likewise usually solid core based.

SUMMARY OF THE INVENTION

Objects of the present invention include providing improved techniques for performing integrated IR and Raman spectroscopic measurements on a gas sample located within a confined volume, extending the path length of a hollow gas sampling structure thereby providing a capability for sensing a broader range of gas species, obtaining complimentary spectroscopic gas species information, reducing the device form factor and increasing the measurement sensitivity.

These and other objects will be apparent based on the disclosure herein.

The present invention provides embodiments of an optical design and device that combines Raman scattering and infrared (IR) absorption spectroscopy for gas detection. This combination offers a broader sensing capability (both Raman and IR spectroscopy) than prior art systems. The complementary spectra enable detection and identification of unknown gas species, which is a significant advancement in the field of gas sensors.

Embodiments of the present invention include a hollow fiber waveguide (HFW) and a metal coated capillary, each possibly but not necessarily in combination with a solid core optical fiber probe which provides robust field deployment. The optical fiber probe may also encompass an optical filter(s). The hollow gas sampling structure embodiment, e.g., acts as an extended optical path length or multi-pass cell that does not require sensitive alignment. The embodiments using a retro-reflection optical design enhance sensitivity by extending the optical interaction path length of the Raman excitation light and the IR light with the gas sample and by increasing the number of Raman and IR product (e.g. photons) collected.

The hollow structures of the present invention function as a fiber optic-based multi-pass optical cavity to increase the light (e.g. photon)/gas interaction path length and as a cylindrical gas cell to confine the gaseous analyte during the measurement to a known volume essential to quantitative measurements. Both functions combined enable low detection limits to be reached in a continuous measurement scenario. A variety of spectroscopic techniques can be used with this hollow cylindrical structure in parallel, but not limited to, Infrared and Raman spectroscopy by coupling of light of differing wavelengths. In addition, the inner surface of the hollow structure can be coated with a single or multiple optical coatings (e.g., (but not limited to) reflective metallic and dielectric layers) optimized to achieve higher throughput and sensitivity.

In an embodiment of the present invention, IR light is delivered to a hollow gas sampling structure that contains the gas analyte, and attenuation of the light intensity as a result of selective absorption by the molecules is detected at the distal end of the waveguide as the light exits the fiber. Using a broadband IR radiation source, usually a frequency resolved spectrum is recorded, while a configuration using and IR laser radiation source may record simply attenuation of the radiation intensity. The gas molecule can be introduced into the core of the hollow structure, e.g., at either or both ends of the structure. For situations, where only one access port is allowed for the sensor, the light delivery and collection can be performed at the same end of the fiber. There is also a need to reduce the weight and size of these sensors for miniaturization. If a particular application requires that tight connections must be made at both ends of the hollow structure for collection of optical signals, gas molecules may be restricted from entering the core on either end. The present invention is designed to resolve all of these issues.

This invention combines Raman and IR spectroscopy in a single fiber-based gas sensor device for the purpose of detecting, identifying, and quantifying low concentration levels of individual gases and gas mixtures. This combination of both Raman scattering and IR absorption spectroscopy in a single optical design produces complementary spectra that function as molecular-level fingerprints of the gaseous species being probed. Together, these signatures enable the identification of unknown gas species. An essential component of embodiments of this invention include a hollow gas sampling structure in which the gas analytes are confined to a predetermined volume and for increasing the interaction path length between the (excitation) light and the gas molecules. This enables detection limits down to the parts-per-million (ppm) and parts-per-billion (ppb) levels to be reached. Also important to some embodiments is the choice of coatings (e.g., but not limited to) aluminum, silver, dielectric, etc.) at the inside of the hollow fiber to minimize optical losses. Coupling of a solid core probe or optical fiber, which delivers excitation light to the hollow structure, is provided by a novel fiber geometry. Important for a remote sensing geometry is a double pass arrangement using a retro reflector to direct the scattered light (Raman) or to further increase the absorption path length of light (IR) traveling back through the hollow structure and into the solid core fiber probe, enabling detection of the signals at the same side as the excitation.

The spectroscopic techniques usable in the present invention include absorption, photo-acoustics, Raman, fluorescence, surface-enhanced Raman, surface-enhanced infrared, and/or coherent anti-Stokes Raman scattering spectroscopy. The hollow structure functions as a confined volume gas sampling structure in which photons from a light source interact with the gas sample to be detected, and which is present inside the hollow structure. The sample can either be in aqueous or gaseous phase, and can be delivered into the structure by either directly pumping or flowing it into the volume, or by natural diffusion, convection, etc. The molecules can be introduced through the ends of the hollow structure, which are open to the surrounding environment. Another embodiment provides porous structures either at specific locations or along the entire hollow gas sampling structure. Some of the hollow structures usable in the invention are cylindrical in shape and have a diameter ranging from hundreds of microns to several millimeters and its length can be up to meters long. The inside of the structure can be coated with a light guiding and/or reflecting layer, e.g., (but not limited to) a metallic or dielectric layer, to enable light to be guided down the length of the hollow structure. The coating also serves to guide the analytical signal (e.g., scatterings). The layer can also be functionalized for directly targeting and/or recognizing molecules, or roughened to enable surface-enhancement features. Light, from a source such, but not limited to, as a quantum cascade laser, diode laser, or a broadband source is efficiently coupled into the hollow structure using, e.g., a focusing lens, microoptics, fiber optic components, or combinations thereof.

The invention can be used in weapons sensors for continuous monitoring and detection of gases, gas mixtures, and identifying unknown gas species. It can be used for quantification of gas species, environmental, monitoring, as a hand held first responder device to identify and locate victims following a natural disaster or terrorist attack based on molecules generated by a victim (e.g., CO2), for homeland security, e.g., as a breath analysis tool for detection of low concentration levels of high explosives handled and inhaled by suspect persons, for breath analysis for radiological exposure assessment, breath analysis for detecting diseases in-vivo (e.g., cancer) and may generally be used as a chemical sensor/detector.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

Figure 1A:
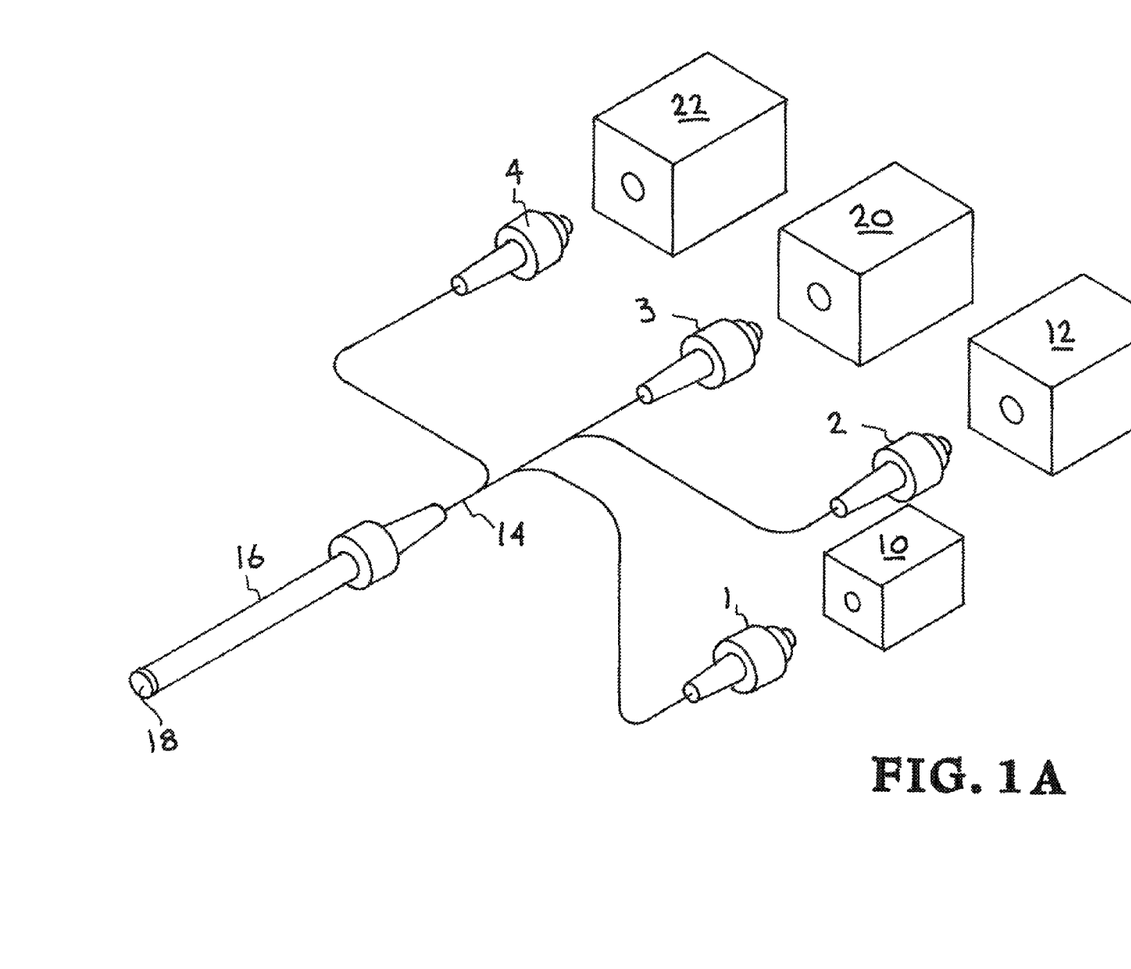
FIG. 1A shows a present invention embodiment and components of a combined Raman scattering and IR absorption spectroscopy hollow gas sampling structure-based gas sensor.
Figure 1B:
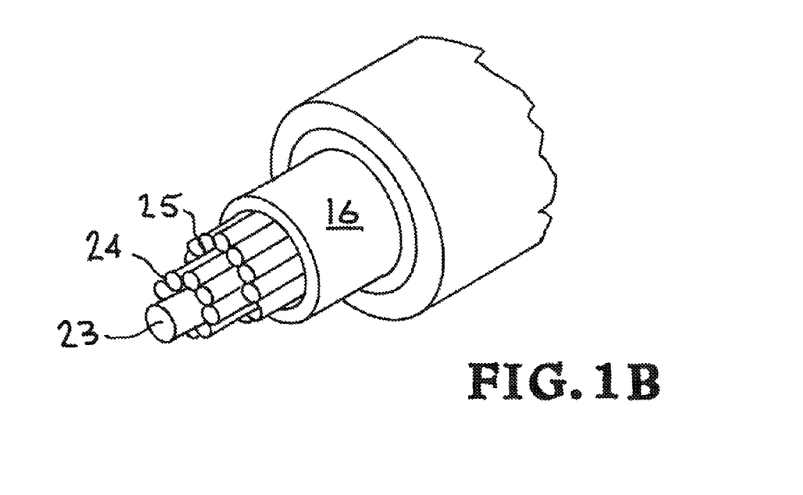
FIG. 1B shows an enlarged view of the distal end of the solid core optical fiber probe with attached hollow gas sampling structure of FIG. 1A.

FIG. 1A illustrates as an example of a present invention design of a gas sensor that combines both Raman scattering and IR absorption spectroscopy for gas detection. Components in this design include a Raman excitation light source 10, an IR illumination light source 12, an optional solid core optical fiber probe 14 (which can consist of fiber optics 1-4, each having a termination. The distal ends of fibers 1-4 may but do not have to terminate into a fiber bundle which delivers light to a hollow structure 16 with optional coatings and filtering as described herein. A retro reflector 18 provides a second pass of light through the hollow gas sampling structure and directs light to, a Raman signal detector 20 and an IR signal detector 22. FIG. 1B shows an enlarged view of the distal end of the solid core optical fiber probe of FIG. 1A. The figure shows a center fiber 23 that can be used to deliver the Raman excitation light. One or more of the surrounding fibers 24 can be used to deliver the IR light. Some or all of the fibers 25 that surround fibers 24 can be used to collect the Raman signal and/or the IR light. The figure further shows a portion of the hollow gas sampling structure 16.

Raman excitation light source 10 can be a laser that emits monochromatic light. The wavelength of the light can range, e.g., (but not limited to) from the UV to the near infrared spectral region (for example, 200 nm-785 nm). The laser power can be, e.g., in the milliwatt range (e.g., about 500 mW). In the exemplary embodiment, monochromatic light is coupled into solid core optical fiber probe termination 1. The fiber in the center (FIG. 1B) delivers the monochromatic laser light while the surrounding fibers are used for collection of Raman and IR light. Optional bandpass and longpass optical filters placed at the fiber ends and also in the spectrometer serve to reduce undesired signals that may interfere with the Raman signal of the gas analyte. Example undesired signals may include residual lines from the excitation laser beam, Rayleigh scattered light, and Raman signals from the fiber material (e.g., (but not limited to) silica Raman scattered light, etc.). The solid core fiber probe can consist of various combinations of fiber bundles (e.g., 1 around 6), 2-fiber, and 24-around-1) with, e.g., one fiber delivering the light and the remaining fibers collecting the Raman signal and IR signals. This solid core fiber bundle is coupled to a hollow gas sampling structure (HFW) 16, which can have a diameter of, e.g., about 1 mm and an internal metal coating (e.g., silver, aluminum). The proper choice of coating can be selected based on the wavelength(s) of the excitation light provided by Raman source 10 and/or IR source 12. The hollow gas sampling structure may contain a gas analyte of interest, which can enter the hollow structure by diffusion through openings in the structure. It is within the hollow structure that the laser beam interacts with the gas sample to generate the Raman scattering and IR light signals. The hollow gas sampling structure functions as a type of multi-pass cell to increase the interaction path length between photons and the gas molecules. The length of the fiber can be varied to optimize this interaction. An exemplary length is 1-2 ft. The retro reflector 18 (e.g., mirror or reflective coating) is used to reflect the excitation light (from source 10 and/or source 12) that is travelling through the hollow gas sampling structure and then back through the same structure for a second pass to increase the interaction path length and to direct the Raman signals and the non absorbed IR light toward the solid core fiber bundle for Raman and IR signal collection. The signal collection fibers deliver the signals to the detectors 12 and 22. These detectors can either or both consist of a wavelength selector (e.g., (but not limited to) a spectrometer) and a sensitive CCD camera, or any other detection device for continuously recording Raman and IR signal.

In the exemplary embodiment shown in FIG. 1A, components for the IR gas sensor include an IR light source 12. This source can be e.g., a broadband light source (e.g., SiC globar) for performing Fourier transform IR spectroscopy, a quantum cascade laser, which emits light at a specific, narrow wavelength and may provide tenability, or a series of quantum cascade lasers, each emitting at different wavelengths. Other IR sources will be apparent to those skilled in the art based on the present disclosure, and are within the scope of the invention. The wavelengths of the light may be, e.g., (but not limited to) in the mid-IR to IR range such as from about 2.5-20 microns. This invention also includes using radiation extending into the far-IR (THz) spectral regime from 20-1000 microns. This light/radiation is coupled into solid core fiber probe proximal end 2 for delivery to the hollow gas sampling structure 16. The solid core fiber of end 2 comprises a material different than the Raman fiber of end 1 because it needs to transmit in the IR wavelength range. The light is coupled into the HFW 16 and is reflected back by the retro reflector 18. The back-reflected light, which is attenuated in intensity because of its absorption by the gas molecules, is collected by the same solid core fiber and sent to the IR detector. In one example, this solid core fiber may be bifurcated in order to split the light away from the direction of the light source and into the IR detector. Alternatively, the solid core IR fiber probe can consist of two or more fibers bundled together, with one fiber delivering the light to the hollow gas sampling structure and the remaining fibers used to collect the attenuated light.

Figure 2:
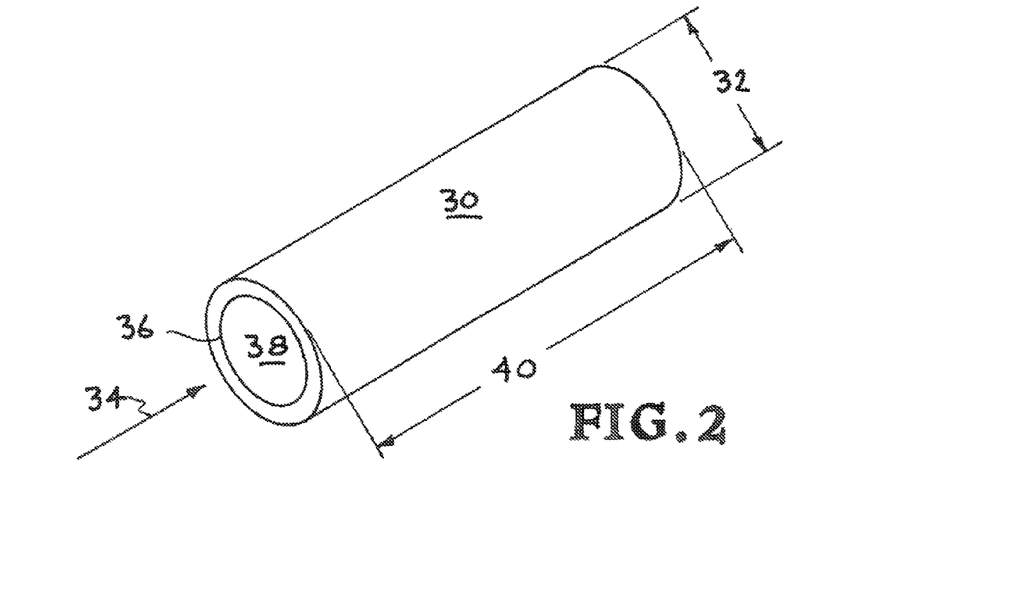
FIG. 2 is a present invention design and dimensions of a hollow cylindrical structure for gas analysis.

FIG. 2 is a schematic of a design and dimensions of a hollow cylindrical structure (such as the hollow gas sampling structure 16) for gas analysis. In FIG. 2 the hollow structure 30 has typical diameter dimensions 32 ranging from tens or hundreds of microns up to several millimeters in diameter. This diameter depends on the coupling conditions of the light 34 into the core of hollow structure 30. They can be fabricated from capillaries or tubing and can be made of a variety of materials such as silica and quartz. The inner surface 36 of this hollow structure can be coated with different layers 38 (e.g., metallic, dielectric, etc.) depending on the wavelength of the light source that is being used. The length 40 of the structure can vary from, e.g., several tens of centimeters to a few meters. This length is usually defined by the practical size restriction of the field sensor. In other situations, the length can be defined e.g., by the optical limitations of the coating. For example, situations may arise in which there is no benefit to having longer and longer structures, because the reflectivity of the coating sets a maximum throughput threshold for the entire structure.

Figures 3A, 3B, 3C:
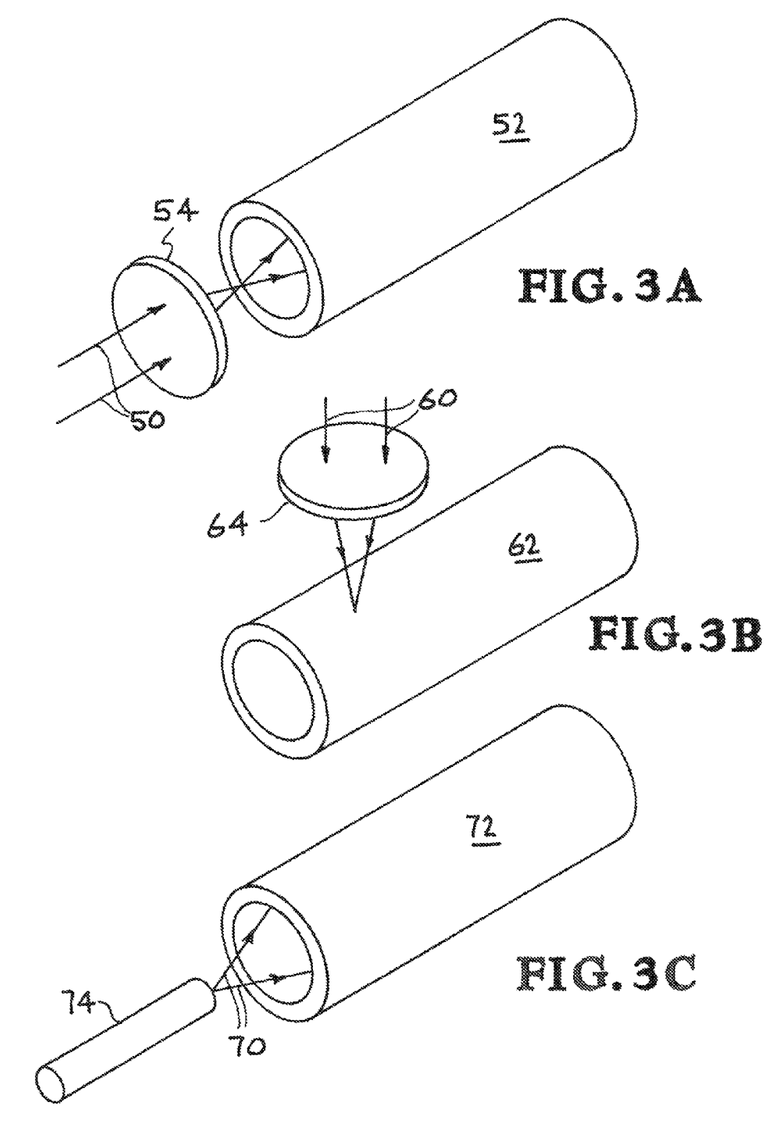
FIG. 3A is a present invention schematic of the coupling of light into a hollow gas sampling structure using a focusing lens.
FIG. 3B is a present invention schematic of the coupling of light into a hollow gas sampling structure using at least one optical fiber.

Light from a source can be coupled into the core of the hollow device using, e.g., a focusing lens or micro-optics (e.g., a GRIN lens, etc.), or direct coupling of light delivered from a solid core fiber. Spectroscopic techniques that can be used with this hollow geometry include Raman and IR, absorption, emission, scattering, photo-acoustics and fluorescence spectroscopy. The light sources can be broadband for applications where an entire spectrum of the analyte is desired, or narrow such as from a diode laser or quantum cascade laser, for applications where absorption or Raman scattering of a specific wavelength of light is required or Raman scattering. The detection of the light can be performed either at the proximal or distal end of the hollow structure, depending on the desired optical configuration of the device. FIG. 3A shows an example means for end coupling light 50 into a hollow gas sampling structure 52 using a focusing lens 54. FIG. 3B shows an exemplary way to side couple light 60 into a hollow gas sampling structure 62 using a lens 64. FIG. 3C shows an exemplary way to side couple light 70 into a hollow gas sampling structure 72 using an optical fiber 74.

Figure 4:
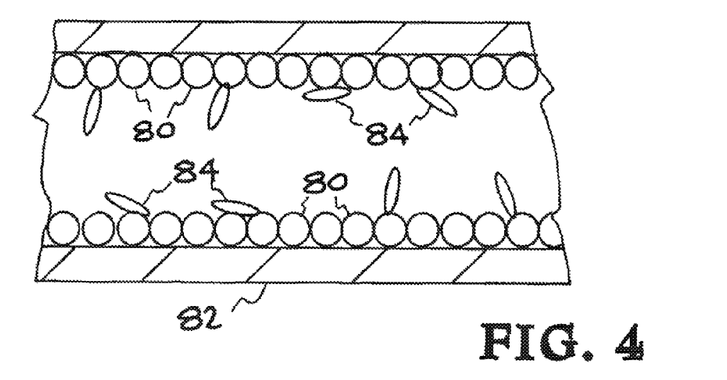
FIG. 4 illustrates a present invention roughened metal coating on the interior of a glass hollow waveguide where the adsorption of molecules to the surface for surface enhanced Raman or IR spectroscopy.

FIG. 4 illustrates an embodiment with a roughened metal coating 80, represented by circles, on the interior of a glass hollow structure portion 82 and the adsorption of molecules 84 to the surface of the coating 80 for performing surface enhanced Raman spectroscopy (SERS) or surface-enhanced Infrared absorption spectroscopy (SEIRA). In this design, the roughened surface may include nanostructures (e.g., metallic) that can efficiently generate surface enhanced Raman or surface enhanced infrared spectra of analytes that adhere or are in molecularly close proximity to the nanostructures. Molecules may also adhere by functionalization of the internal hollow gas sampling structure surface with appropriate recognition or enrichment elements or by natural adhesion to the bare surface. In addition, nanostructures may also be fabricated at the surface of the coating to perform surface plasmon resonance (SPR) spectroscopy. Other means for surface enhancement will be apparent to those skilled in the art based on this disclosure, and are within the scope of the present invention.

Figure 5:
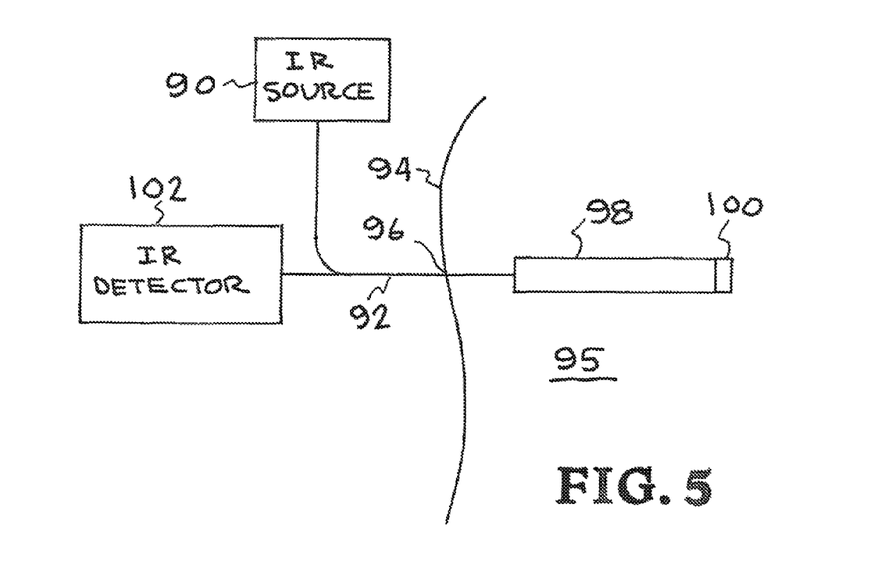
FIG. 5 is a present invention schematic of an optical configuration of a double pass IR gas sensor.

FIG. 5 shows a schematic of an optical configuration of an exemplary embodiment of a double pass IR gas sensor portion of the present invention. The fiber-based sensor has one port to which the fiber is connected and the sensor is placed in an enclosed chamber in which the gas molecules are present. Detection of signals from the molecules must be achieved only through this one port and signals are to be collected using the same single fiber probe. In the figure, infrared source 90 is input into fiber 92, which is coupled through a boundary 94 to an enclosed environment 95 of interest via a single access port 96. The fiber may be coupled to a second fiber on the environment side of boundary 94, or fiber 92 can be passed through an opening in the boundary. The distal end of fiber 92 is connected to a hollow gas sampling structure 98 that includes a retro reflector 100. The hollow gas sampling structure can include any means for surface enhancement as described herein or that will be apparent to those skilled in the art based on this disclosure. Light reflected by the retro reflector will make a second pass through the hollow gas sampling structure, and propagate back in fiber 92 to an IR detector 102. Gas from environment 95 can enter the hollow structure 98 though openings in the structure as discussed herein.

Figure 6:
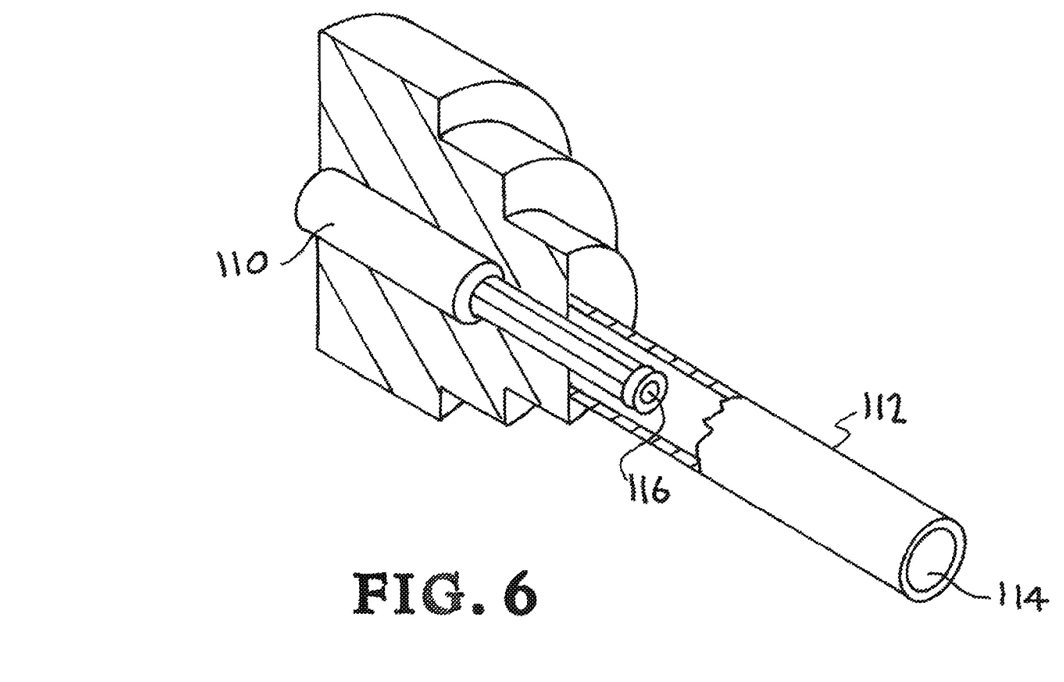
FIG. 6 is a present invention optical design of a solid core fiber probe connected to a hollow gas sampling structure with retro reflector at the HFW end.

An example of one implementation of the retro reflector double pass design is shown in FIG. 6. The solid core fiber probe 110 is connected to the hollow gas sampling structure 112 which includes a retro reflector 114 at the hollow structure end. Light is coupled into the hollow structure using either a focusing element (e.g., lens 116) or direct coupling between the hollow structure and a standard solid core optical fiber probe. The hollow gas sampling structure may include a highly reflective inner coating (e.g., Al, Ag, Au, etc.). The light propagates down the hollow gas sampling structure and interacts with the gas molecules that are present within the core. The retro reflector at the end of the fiber reflects light signals back towards the entrance end of the fiber. The retro reflector can be a highly reflective flat mirror or a curved mirror that maximizes the reflected light back to the hollow structure. The coating can be designed to reflect only one specific wavelength or a broad spectral range, depending on the light source that is used. Gas molecules can enter the hollow gas sampling structure, e.g., (but not limited to) through the gaps between the retro reflector and the hollow structure or through gaps between the hollow structure and the solid core optical fiber probe. Light that reaches the entrance of the hollow gas sampling structure will have made a double pass through the hollow structure, which doubles the interaction length between the photons and the molecules without needing to double the length of the HFW. The light is then collected by the same optical fiber probe, which can be split off by using e.g., a bifurcated optical fiber or a beamsplitter, and propagated to a detector.

The foregoing description of the invention has been presented for purposes of illustration and description and is not intended to be exhaustive or to limit the invention to the precise form disclosed. Many modifications and variations are possible in light of the above teaching. The embodiments disclosed were meant only to explain the principles of the invention and its practical application to thereby enable others skilled in the art to best use the invention in various embodiments and with various modifications suited to the particular use contemplated. The scope of the invention is to be defined by the following claims.

We claim:

1. An apparatus, comprising:
    a hollow gas sampling structure having a first end, a second end, a diameter ranging from at least 200 micrometers to no more than 3 millimeters, a reflector located at said second end, an opening configured wherein a gas can freely but not forcibly migrate into and out of said structure and a reflective inner wall comprising a reflective material selected from the group consisting of a metal and a dielectric, wherein said reflective material is reflective and not absorbing of (i) Raman excitation light and Raman light having a wavelength within a range from UV to visible and (ii) infrared (IR) radiation having a wavelength within a range from 3 μm to 20 μm;
    a fiber optic bundle comprising a first distal end operatively and proximately connected to said first end, wherein said fiber optic bundle further comprises:
    a multimode first fiber optic configured for transmitting said Raman excitation light into said gas to produce Raman light generated in said gas, wherein said first fiber optic comprises a first fiber optic proximal end and a first fiber optic distal end, wherein said first fiber optic distal end terminates at said first distal end;
    a multimode second fiber optic configured for transmitting said IR radiation into said gas to produce attenuated IR radiation, wherein said second fiber optic comprises a second fiber optic proximal end and a second fiber optic distal end, wherein said second fiber optic distal end terminates at said first distal end, wherein said second fiber optic is further configured for collecting said attenuated IR radiation;
    a multimode first collection fiber configured for collecting said Raman light, wherein said first collection fiber optic comprises a first collection fiber optic proximal end and a first collection fiber optic distal end, wherein said first collection fiber optic distal end terminates at said first distal end;
    a first source of said Raman excitation light, wherein said first source is configured to direct said Raman excitation light into said first fiber optic proximal end;
    a second source of said IR radiation, wherein said second source is configured to direct said IR radiation into said second fiber optic proximal end;
    a Raman light detector configured to receive said Raman light from said first collection fiber optic proximal end; and
    an IR radiation detector configured to receive said attenuated IR radiation.

2. The apparatus of claim 1, wherein said IR radiation detector is configured to receive said attenuated IR radiation from said second fiber optic proximal end.

3. The apparatus of claim 1, wherein said bundle further comprises as multimode second collection fiber configured for collecting said attenuated IR radiation, wherein said second collection fiber optic comprises a second collection fiber optic proximal end and a second collection fiber optic distal end, wherein said second collection fiber optic distal end terminates in proximity with said first distal end, and wherein said IR radiation detector is configured to receive said attenuated IR radiation from said second collection fiber optic proximal end.

4. The apparatus of claim 1, further comprising a lens located such that said Raman excitation light and said IR radiation exiting said first distal end must propagate through said lens before interacting with gas located within said hollow gas sampling structure.

5. The apparatus of claim 1, further comprising a non-holographic filter located such that said Raman excitation light and said IR radiation exiting said first distal end must propagate through said filter before interacting with gas located within said hollow as sampling structure.

6. The apparatus of claim 1, wherein said mirror comprises a retroreflector.

7. The apparatus of claim 1, wherein said hollow gas sampling structure comprises a geometry selected from the group consisting of a tube and a groove in a planar waveguide.

8. The apparatus of claim 1, wherein said metal is selected from the group consisting of silver, gold, aluminum, platinum and rhodium and wherein said dielectric is configured within one or more layers of reflective and refractive coatings.

9. The apparatus of claim 1, wherein the inner surface of said hollow gas sampling structure comprises a feature selected from the group consisting of a roughened surface and nanostructures.

10. A method, comprising:
    providing the apparatus of claim 1;
    directing said Raman excitation light into said first fiber optic proximal end such that it propagates through said multimode first fiber optic to exit said first fiber optic distal end and enter said hollow gas sampling structure to interact with said gas and produce said Raman light;

collecting said Raman light into said first collection fiber optic distal end such that it propagates through said first multimode collection fiber and exits said first collection fiber optic proximal end;

detecting said Raman light that exits from said first collection fiber optic proximal end;

directing said IR radiation into said second fiber optic proximal end Such that it propagates through said multimode second fiber optic to exit said second fiber optic distal end and enter said hollow gas sampling structure to interact with said gas to produce said attenuated IR radiation; and detecting said attenuated IR radiation.

11. The method of claim 10, wherein the step of detecting said attenuated IR radiation comprises receiving into an IR radiation detector said attenuated IR radiation that exits from said second fiber optic proximal end.

12. The method of claim 10, wherein said apparatus further comprises a multimode second collection fiber configured for collecting said attenuated IR radiation, wherein said second collection fiber optic comprises a second collection fiber optic proximal end and a second collection fiber optic distal end, wherein said second collection fiber optic distal end terminates in proximity with said first distal end, wherein the step of detecting said attenuated IR radiation comprising receiving into an IR radiation detector said attenuated IR radiation that exits from said second collection fiber optic proximal end.

13. The method of claim 10, wherein said apparatus further comprises a lens located between said first distal end and said gas.

14. The Method of claim 10, wherein said apparatus further comprises a filter located between said first distal end and said gas.

15. The method of claim 10, wherein said mirror comprises a retroreflector.

16. The method of claim 10, wherein said hollow gas sampling structure comprises a geometry selected from the group consisting of a tube and a groove in a planar waveguide.

17. The method of claim 10, wherein said metal is selected from the group consisting of silver, gold, aluminum, platinum and rhodium and wherein said dielectric is configured within one or more layers of reflective and refractive coatings.

18. The method of claim 10, wherein the inner surface of said hollow gas sampling structure comprises a feature selected from the group consisting of a roughened surface and nanostructures.

19. The method of claim 10, further comprising analyzing at least one of said Raman light and said attenuated IR radiation to determine at least a portion of the composition of said gas sample.

20. The Method of claim 10, further comprising reflecting from said reflector at least a portion of one of said Raman excitation light and said IR radiation.

\* \* \* \* \*